United States Patent [19]

Merril

[11] 4,405,720
[45] Sep. 20, 1983

[54] SILVER STAINS FOR PROTEIN IN GELS
[75] Inventor: Carl R. Merril, Rockville, Md.
[73] Assignee: The United States of America as represented by the Department of Health and Human Services, Washington, D.C.
[21] Appl. No.: 339,886
[22] Filed: Jan. 18, 1982

Related U.S. Application Data

[63] Continuation-in-part of Ser. No. 240,577, Mar. 4, 1981, abandoned.
[51] Int. Cl.$^3$ ............................................. G01N 33/68
[52] U.S. Cl. ...................................... 436/86; 436/169; 436/174; 436/905
[58] Field of Search ...................... 23/230 B, 902, 912; 436/86, 169, 174, 905

[56] References Cited

U.S. PATENT DOCUMENTS 3,873,433  3/1975  Seidel et al.
4,167,467  9/1979  Golias.

OTHER PUBLICATIONS

C. R. Merril et al., Anal. Biochem., 110(1), 201–207, (Jan. 1, 1981).
Kerenyi, et al., "A Highly Sensitive Method for Demonstrating Proteins in Electrophoretic, Immuno-electrophoretic and Immuno-diffusion Preparations", Clin. Chim. Acta, 38, 465–467, (1972).
Kerenyi, et al., "Uber Probleme der Quantitiven Auswertung der mit Physikalischer Entwicklung Versilberten Agarelektrophoretogramme", Clin. Chim. Acta, 47, 425–436, (1973).
Veerheecke, "Agargel Electrophoresis of Unconcentrated Cerebrospinal Fluid", J. Neurol., 209, 59–63, (1975).
Karcher, et al., "Cerebrospinal Fluid Proteins Electrophoresis without Prior Concentration", Acta nuerol. Belg., 79, 335–337, (1979).
Switzer, et al., "A Highly Sensitive Silver Stain for Detecting Proteins and Peptides in Polyacrylamide Gels", Anal. Biochem, 98, 231–237, (1979).
Merril, et al., "Trace Polypeptides in Cellular Extracts and Human Body Fluids Detected by Two-Dimensional Electrophoresis and a Highly Sensitive Silver Stain", Proc. Natl. Acad. Sci. U.S.A., 76, 4335–4339, (1979).
Oakley, et al., "A Simplified Ultrasensitive Silver Stain for Detecting Proteins in Polyacrylamide Gels", Anal. Biochem. 105, 361–363, (1980).

*Primary Examiner*—Sidney Marantz
*Attorney, Agent, or Firm*—Holman & Stern

[57] ABSTRACT

A silver stain method for polypeptides in gels comprising the sequential steps of photo-reversing the polypeptide-gel by treatment with an oxidizing agent, forming a latent stain image by treating the polypeptide-gel with a photosensitive salt, and developing the stain image by treating the polypeptide-gel with a reducing agent.

16 Claims, 10 Drawing Figures

SILVER STAINS FOR PROTEIN IN GELS

This is a continuation-in-part application of Ser. No. 06/240,577 filed Mar. 4, 1981, now abandoned.

BACKGROUND OF THE INVENTION

1. Field of the Invention

This invention relates to improved ultra-sensitive metallic silver stains for polypeptides, especially when fixed in synthetic gels, particularly polyacrylamide gels.

2. Description of the Prior Art

Detection and characterization of polypeptides is of fundamental importance to many areas of biology and clinical medicine. In some endeavors, such as genetic screening for mutational events, monitoring for pathophysiologic changes in disease states, and the diagnosis of genetic diseases, the efficiency of the search is directly proportional to the number of polypeptides that can be detected and characterized in cellular extracts of body fluids. Additionally polypeptides, hormones, etc., that are present in trace amounts are often of great importance for various medical reasons.

Electrophoresis (defined generally as the movement of charged particles in solution under the influence of an electrical field), is a primary laboratory detection and characterization technique, especially useful for polypeptides and other micromolecules, such as nucleic acids. It is also useful in separating small particles such as viruses, cells, sub-cellular organelles and organic molecules such as steroids and amino acids.

Continuing developments in two-dimensional gel electrophoresis have provided the capability of resolving thousands of polypeptides from complex biological mixtures. However, the inability to detect polypeptides present in low concentration has limited the application of this technology, particularly in clinical screening for pathological states, endocrinology, mammalian metabolism, developmental biology, and immunology.

Because the improved gel electrophoretic techniques greatly increase polypeptide resolution, visual detection methods employing conventional polypeptide dyes are no longer adequate.

The most commonly used conventional polypeptide stain is Coomassie Blue, which may be considered as a prototype. Dyes of this type are mainly dependent upon the electrostatic attraction between dye and polypeptide, stabilized by van der Wall's forces. In fact, Coomassie Blue and a variety of other dyes exhibit particular affinities for polypeptides of specific charge. Coomassie Blue, an acidic dye, stains basic polypeptides most intensely, while crystal violet is the most effective stain for acidic polypeptides. Other dyes for which quantitative aspects of staining have been investigated include Amido Black, Fast Green, and $Fe^{2+}$-bathophenanthroline sulfonate. In contrast, the Remazol Brilliant Blue R method depends on a covalent bond between dye and polypeptide. With Coomassie Blue, linearity has been found, by staining for 30 minutes in 1.5 mm diameter gels, in the polypeptide concentration range of 0.05-2 $\mu$g using the parameter of relative spot area. Staining for 60 rather than 30 minutes may result in an increase in the slope of the area/concentration relationship and nonlinearity due to saturation above 1 $\mu$g. Fluorescamine can react with terminal and $\epsilon$-amino groups of polypeptides in gels to achieve a sensitivity at least equal to that of Coomassie Blue, with linearity from 1 to 7 $\mu$g "per spot". MDPF (2-methoxy-2-4-diphenyl-3(2H)-furanone) may be used to label polypeptides fluorescently prior to electrophoresis, with linearity from 10 ng to 10 $\mu$g of protein. However fluorescent staining of polypeptides prior to electrophoresis may alter their electrophoretic patterns.

An assortment of other techniques which do not require modification of polypeptides prior to electrophoresis also exist. These include densitometric scanning for absorbance at 280 nm, binding of radiolabelled or fluorescent ligands such as concanavalin A to glycoproteins, binding of antisera to polypeptides at the gel surface, and staining of specific polypeptide moieties including carbohydrate sidechains with PAS, sulfhydryl groups with 5,5'-dithiobis (2-nitrobenzoic acid), copper polypeptides with cyanide-tetrazolium, cadmium polypeptides with dipyridyl-ferrous iodide and $Ca^{2+}$-polypeptides with $^{45}Ca$ autoradiography.

Radioactive detection techniques offer a higher degree of sensitivity than the stains but are often impractical to use. In vivo radiolabelling may alter cellular metabolism and it may be impossible to label certain human polypeptides. In vitro radiolabelling has the disadvantage that it might alter the electrophoretic mobility of polypeptides. Furthermore, radioactive reagents sometimes prove too expensive and long exposure to detect trace polypeptide may result in the problem of "autoradiographic spreading".

Polypeptides labelled with a radioactive precursor may be detected by autoradiography and/or fluorography, which have been standardized and used quantitatively. A set of radiographic standards placed next to the gel during exposure of the film may facilitate quantification. Fluorography requires impregnation of the gel with a scintillation fluor and is of greatest use when a low energy beta emitter has been used for labelling or when an increase in sensitivity of detection is required. Quantitative use of fluorography requires prefogging of the film. Recently, in vitro methods for chemically radiolabelling polypeptides prior to electrophoresis have been described. These include the reductive methylation of $\epsilon$-amino groups of lysyl residues and $\alpha$-amino groups of N-terminal amino acids which can be accomplished with formaldehyde and sodium cyanoborohydride. Carbon$^{14}$ formaldehyde or $^3H$ sodium cyanoborohydride may be used as the radiolabel. N-succinimidyl [2,3-$^3H$]propionate can be used to label covalently terminal and $\epsilon$-amino groups either in vivo or in vitro. All of these methods may, unfortunately, alter the labelled polypeptides' mobility.

The above staining methods, moreover, are difficult to perform, hazardous, time consuming, and unless the polypeptides are heavily labeled, lack the sensitivity to detect proteins present in low or trace concentrations. A problem arises, for example, with body fluids, such as cerebrospinal and amniotic fluids, which are often difficult to obtain in quantity and frequently contain certain abundant proteins which cause distortion of electrophoretic patterns when sufficient sample is analyzed to observe specific trace polypeptides.

Recently, highly sensitive silver stain methods for polypeptides in polyacrylamide gels have been developed. These methods have the disadvantages of being too wasteful of silver and/or being too complicated, and in most instances are less sensitive or reproducible than the improved method of this invention, although more sensitive than non-silver stains.

Kerenyl and Gallyas, in "A Highly Sensitive Method for Demonstrating Proteins in Electrophoretic, Immunoelectrophoretic and Immuno-diffusion Preparations", *Clin. Chim. Acta,* 38, 465-467 (1972) discloses a silver stain for proteins in agar gel in which the gel is immersed in potassium ferrocyanide, and then in a two solution developer containing sodium carbonate and water in the first solution and ammonium nitrate, silver nitrate, tungsto-silicic acid, and formaldehyde in the second solution. The possibility of using polyacrylamide gel is mentioned.

Kerenyi and Gallyas, in "Über Probleme der Quantitiven Auswertung der mit Physikalischer Entwicklung Versilberten Agarelektrophoretogramme", *Clin. Chim. Acta,* 47, 425-436 (1973) continued the study of the silver stain disclosed in 1972, above. Artifacts developed during the staining, whose avoidance is discussed.

Veerheecke, in "Agargel Electrophoresis of Unconcentrated Cerebrospinal Fluid", *J. Neurol.,* 209, 59-63 (1975) discloses silver staining in agar gel utilizing two solutions after immersion of the protein-containing gel in potassium ferrocyanide. The first solution contains sodium carbonate in water, the second solution contains ammonium nitrate, water, formaldehyde, and tungsto-silicic acid as well as silver nitrate. The results reported are mixed, although generally favorable. Mention is made that the method of Kerenyi and Gallyas (1972), supra, of which this was a replication, did not appear to have found widespread acceptance, possibly because discrete bands in the gamma region of the electropherogram could not be detected and because numerous artifacts were experienced. Veerheecke himself experienced difficulties with bands in several regions.

Karcher, Lowenthal and Van Soom, in "Cerebrospinal Fluid Proteins Electrophoresis without Prior Concentration", *Acta nuerol. Belg.,* 79, 335-337 (1979), discloses silver staining utilizing two solutions after immersion of the protein-containing gel in potassium ferrocyanide. The first solution contains sodium carbonate, the second solution contains ammonium nitrate, water, formaldehyde, and tungsto-silicic acid as well as silver nitrate. The disclosure concludes that the stain is comparable to that obtained for conventional electrophoresis staining with amido-black, working with concentrated cerebrospinal fluid.

Switzer, Merril and Shifrin, in "A Highly Sensitive Silver Stain for Detecting Proteins and Peptides in Polyacrylamide Gels", *Anal. Biochem,* 98, 231-237 (1979), discloses a silver stain in which the proteins are fixed by soaking of the gel in various methanol/acetic acid mixtures for at least 2.5 hours, soaking the gel in a paraformaldehyde solution for 0.5 hours, placing the gel in a cupric nitrate/silver nitrate solution for at least 0.5 hours, placing the gel in a diammine solution (a mixture of silver nitrate, NaOH, $NH_4OH$, and ethanol) for 10 min., and twice reducing the gel stain with formaldehyde and citric acid. The stain was found to be 100 times more sensitive than Coomassie Blue and comparable to autoradiography.

Merril, Switzer, and Van Keuren, in "Trace Polypeptides in Cellular Extracts and Human Body Fluids Detected by Two-Dimensional Electrophoresis and a Highly Sensitive Silver Stain", *Proc. Natl. Acad. Sci. U.S.A.,* 76, 4335-4339 (1979), utilized the stain disclosed by Switzer, Merril and Shifrin in *Anal. Biochem,* (1979). Some potential clinical applications were demonstrated as well as that the stain was more sensitive than Coomassie Blue, and less expensive and more rapid than autoradiography.

Oakley, Kirsch and Morris, in "A Simplified Ultrasensitive Silver Stain for Detecting Proteins in Polyacrylamide Gels", *Anal. Biochem.* 105, 361-363 (1980), which was published less than one year prior to filing the application for this patent in the United States, discloses an adaptation of the silver stain first disclosed by Switzer, Merril, and Shifrin (1979), supra. The disclosed process utilizes (1) soaking the gel in glutaraldehyde for 30 minutes, (2) rinsing and soaking the gel in water for at least 2 hours, (3) adding ammoniacal silver solution (a mixture of $NH_4OH$, NAOH, and $AgNO_3$), (4) transferring the gel to a mixture of citric acid and formaldehyde, and (6) washing in water for at least 1 hour. The stated advantages are simplification of the original procedure, elimination of the cupric-silver nitrate step, and reduction of the amount of silver required. In an attempted replication of this method in connection with the present invention, a significant reduction (about 50%) in sensitivity was observed when the stain method of Oakley, Kirsch and Morris, supra, was compared with that of the improved method of this invention.

No patents are known which disclose silver stains for proteins or which are more relevant than the foregoing monographs.

U.S. Pat. No. 3,873,433 does not disclose silver stains, but does disclose protein staining by the formation of complex organic salts with bivalent elements such as calcium and magnesium.

U.S. Pat. No. 4,167,467 does not disclose silver stains, but does disclose the quantification of lipoprotein free cholesterols using a cholesterol oxidase substrate by enzymatic determination.

SUMMARY OF THE INVENTION

This invention provides improved silver stain methods capable of detecting as little as 0.01 $ng/mm^2$ of polypeptide The methods are analogous to photographic chemistry and comprise the sequential steps of: (1) fixing the polypeptide; (2) photo-reversal using an oxidant; (3) latent image formation, preferably with silver nitrate; and (4) image development to afford a visible stain. The improved silver stain methods of this invention find utility in: clinical and laboratory examination of blood-derived and other polypeptides separated by electrophoresis; prenatal diagnosis of fetal abnormalities by examination of amniotic fluid; diagnosis of central nervous system diseases by analysis of polypeptide patterns in spinal fluid; visualization and quantitation of polypeptides hormones, and analysis of cellular protein patterns for physiological and/or patho-physiological studies; and many other applications in which the detection and/or quantitation of proteins or polypeptides is desired.

All gel compositions suitable for use in electrophoresis may be used in this invention. Typical gels are polyacrylamide, agarose, and cellulose acetate. Polyacrylamide is preferred, because both cellulose acetate and agarose gels when used with the method of this invention give brownish backgrounds (agarose being somewhat darker). If the brownish backgrounds can be avoided, all of these gels would be suitable.

While the stain methods of this invention find their primary utility in connection with staining polypepyides on gels, the same stain methods (sometimes without the fixing step) are also useful in conducting protein assays for polypeptides filtered from source materials and for histological-type stains of tissue slices such as in biopsies.

DESCRIPTION OF THE PREFERRED EMBODIMENTS

Figure 1:
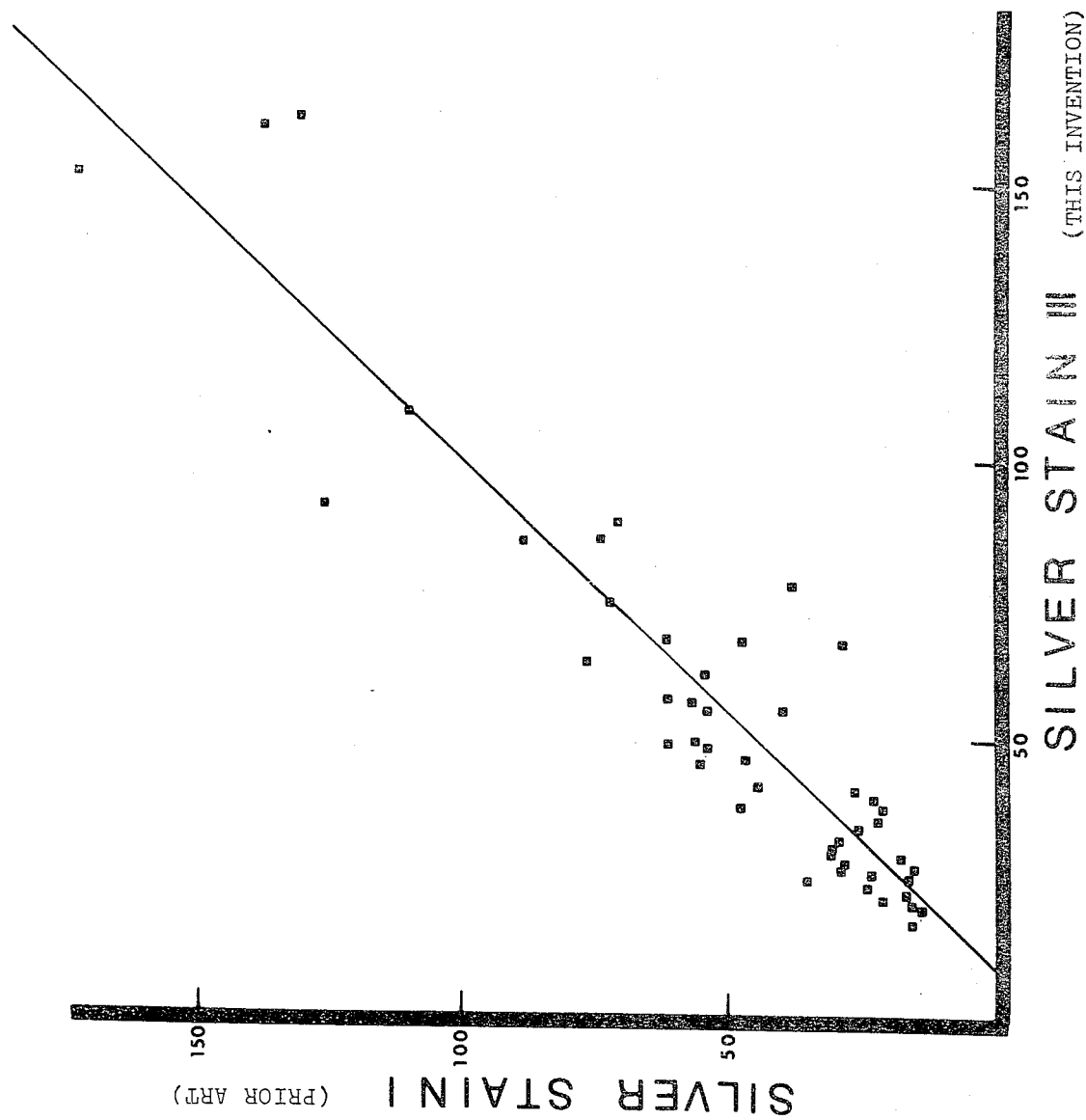
FIG. 1 is a graph comparing the sensitivity of the improved stain according to this invention with a histologically derived silver stain according to Switzer, Merril and Shifrin (1979).

The improved silver stain method of this invention comprises the four basic sequential steps of (1) washing and fixing, (2) photo-reversal, (3) latent image formation, and (4) image development. The invention method may be used in connection with gel electrophoresis, polypeptide assays, and tissue staining. Because of the sensitivity of the silver stains of this invention, the method is most useful in conjunction with electrophoresis, especially two-dimensional electrophoresis.

Specifically, in conjunction with electrophoresis using polyacrylamide gels, the method of this invention is as follows.

1st Step (washing and fixing). After the sample believed to contain polypeptides has been introduced into the gel in a conventional manner, it is necessary to "fix" the polypeptides in the gel and to elute substances from the gel which could interfere with the staining procedure. Examples of substances to be eluted are ampholytes used in the isoelectric focusing step of two-dimensional electrophoresis, reducing substances in electrophoretic buffers, and detergents used in electrophoresis (such as sodium dilauryl sulfate). A washing and fixing step is conventional in all polypeptide-gel staining methods, but is of particular importance where small quantities of polypeptides are present. Any of the conventional fixatives may be used, for example, glutaraldehyde, oxides of heavy metals such as mercury, lead, and osmium, formaldehyde, paraformaldehyde, trichloroacetic acid, and acetic acid. However, glutaraldehyde and heavy metal oxides pose health hazards and are therefore least preferred. Trichloroacetic acid (10%), acetic acid, formaldehyde, or paraformaldehyde are preferred fixatives, but all of these must be washed out of the gel prior to staining, usually with methanol or ethanol. The most preferred fixative is an aqueous mixture of ethanol and/or methanol (about 10–50%) and acetic acid (about 5–20%), with about 10% ethanol and about 15% acetic acid being optimum. The effect of fixatives is not accurately known. The above fixing agents have been employed in both histology and protein electrophoresis for years. Without current quantitative methods utilizing external and internal standard proteins with the gels, it is at least known that the relative concentrations of proteins remain constant with the above fixatives. Typically, the gels were fixed by immersion in the fixative for a period of about 5–15 minutes, and immersion in fresh fixer was then repeated up to 3 times. When using a fixative other than the acetic acid-methanol and/or ethanol mixture, this was followed by rinsing, preferably with methanol and/or ethanol. Where the most preferred fixative of an acetic acid-methanol and/or ethanol mixture is used, rinsing is not necessary.

2nd Step (photoreversal). After fixation, the polypeptide-gel is treated with an oxidizing agent to effect "photoreversal" and avoid silver staining of non-polypeptides. Suitable agents include dichromates, potassium permanganate, molecular oxygen, potassium ferricyanide, iodine, and quinone, of which acid dichromates, potassium dichromate and molecular oxygen are preferred. Potassium dichromate is particularly preferred. Potassium ferricyanide was originally tried in this invention, but it was discovered to lack sensitivity. Empirical testing indicated that 0.03 M potassium dichromate yielded the best results. While sublimate dichromate fluids are known in histological staining [see Lillie and Fullmen, "Histopathologic Technic and Practical Histochemistry", 4th ed., McGraw-Hill Book Co., New York (1976) at p. 54], the rationale of their use is quite different from that of this invention. Typically, this step is effected by soaking the fixed polypeptide-gel for about 3–10 minutes (preferably about 5 minutes), preferably in an aqueous solution of potassium dichromate and a small amount of nitric acid. A solution of about 0.03 M potassium dichromate and about 0.0015–0.03 (preferably about 0.0016) N nitric acid is most preferred. In a generally less preferred embodiment, this step may be followed by rapidly rinsing the gel in deionized water.

3rd Step (latent image formation). At this point, the polypeptide-gel is immersed in a photosensitive salt solution, and optionally subjected to actuating irradiation. Silver, gold, platinum, paladium and/or iridium salts may be used, although silver salts are preferred because they are more available and less costly. Silver nitrate is the most preferred salt. The concentration of the salt to be used is inversely (but not proportionally) dependent upon the thickness of the gel. Thus, an ultra-thin gel of 0.01 mm or less requires higher concentrations of the utilized metallic salt, while thicker gels require less. Typically, with a polyacrylamide gel of 0.8 mm thickness, a 0.01 M aqueous silver nitrate solution was empirically found to be most effective. With the proper concentration of oxidizing agent (such as dichromate) in above step 2, light or other irradiation is not required in step 3. In fact, light may be detrimental in that it increases the background. For this reason, it is preferred to prepare the stain in the dark or with a red safety light such as that used in a photographic darkroom. This procedure is analogous to photochemical reversal in photography, wherein the proper oxidizing reagent may permit photoreversal without exposure to light. By analogy, most commercial photoreversal procedures (such as in the production of color slide film) is totally a chemical process and does not utilize light or other irradiation actuation.

The use of light irradiation may be possible and even preferred under certain conditions, such as when the gel thickness is greater than about 1 mm, or when staining certain organic polymers such as DNA. The irradiation may be in any conventional manner and must be sufficient to effect the photochemical reaction. Light radiation from actinic through infrared and/or heat has been found to be effective. When used, the irradiation is preferably during the first minutes of the immersion in the photosensitive salt, to produce maximum sensitivity. Typically, a bright uniform light source such as a 160 watt fluorescent grid lamp which emits light equivalent to a 1,500 watt tungsten source may be used. When a saturating light source of this intensity was used, a 5 minute exposure was found to be adequate. In one instance, when the use of the intense light source was omitted and the polypeptide-gel was subjected to the ambient light and heat of the laboratory, the sensitivity of the staining method (as measured by polypeptide spot densities) was reduced by more than 50%. The immersion of the polypeptide-gel in the silver nitrate solution should be for about 10-30 minutes, preferably about 20 minutes. If a radiation source of sufficient intensity is used, the irradiation may be for only a part of the immersion time, although it may be just as convenient to arrange the silver nitrate immersion time and irradiation time so that they are equal and simultaneous.

4th Step (image development). The polypeptide-gel is then removed from the photosensitive salt solution and optionally rinsed, after which it is subjected to a reducing agent or image developer. The photosensitive salt solution may be recycled by monitoring it and restoring it to the desired concentration. Many developers known in photography may be used, including metallic compounds of iron, tungsten, vanadium and molybdenum, and organic compounds including hydroquinone, pyrogallol, p-aminophenol, p-phenylenediamine, paraformaldehyde, and formaldehyde. Of these, the organic compounds are preferred, and formaldehyde and/or paraformaldehyde are most preferred. When formaldehyde and/or paraformaldehyde are used, it is advantageous to employ it as a mixture with an alkalizing agent, which typically may be sodium carbonate or sodium metaborate. As latent image development may continue until the polypeptide-gel is subjected to the reducing agent, it is advisable and preferred to immerse the polypeptide-gel in the reducing agent immediately it is removed from the photosensitive salt. This will prevent loss of the photosensitive-derived metal in the gel which may result in desensitization. Specifically, after removal from the photosensitive salt solution, the protein-gel should immediately be immersed in the reducing agent for about 10-20 minutes. When using formaldehyde and/or paraformaldehyde, a typical reducing solution would be an aqueous mixture of 0.3 M sodium carbonate and 0.5 ml of formaldehyde per liter. When using such a reducing solution, it is preferable to rinse the polypeptide-gel immediately after removal from the photosensitive salt solution in a first portion of the reducing solution and then to immerse the polypeptide-gel in a second portion of the same solution for about 10-20 minutes, accompanied by gentle agitation. The time of this latter immersion may vary and should be until the stain reaches the desired intensity, usually about 15 minutes. When the staining is complete, the reducing (developer) solution is discarded and the polypeptide-gel is washed thoroughly with distilled water. Optionally, and preferably, the polypeptide-gel is immersed in an acid solution immediately it is removed from the reducing solution and prior to washing. The acid solution may be an aqueous solution of acetic, citric, or hydrochloric acids, acetic acid (1-3%) being preferred. The acid solution acts to stop the stain development and should be used for about 5 minutes.

Continued experimentation with the photochemical silver stains of this invention has revealed that sensitivity to trace proteins was primarily due to diffusion of silver out of the gel during the above image development step. This can be overcome by a recycling stain procedure, according to the following embodiment.

After the image development has been stopped by immersing the gel in the acid solution (optionally followed by one or two repeated acid solution immersion - washes), the 3rd (latent image formation) and 4th (image development) Steps are repeated. This recycling from the photosensitive salt step onward, corrects for depletion of the silver caused by diffusion of the silver out of the gel during the image development. With gels 1 mm thick, the density of the silver deposited in each band or spot reaches a maximum in about 20 minutes in the sodium carbonate/formaldehyde solution. Addition of fresh sodium carbonate/formaldehyde will not enhance the density of the spots at this point. However, by recycling, (replacing the silver nitrate), additional density can be achieved. If polypeptides require further staining, one or more further recycling procedures can be conducted, although background darkening becomes a problem with continued recycling.

Applications of this Invention include:

(1) Routine examination of blood polypeptides separated by electrophoresis on gels. Due to its sensitivity and linear relationship with polypeptide concentration, the stain method of this invention can be used to assay polypeptide abnormalities or pathologies (such as may occur in liver and heart disease).

(2) Prenatal diagnosis of fetal abnormalities by detecting aberrant polypeptide patterns in amniotic fluids which can be correlated with genetic and developmental abnormalities.

(3) Diagnosis of diseases of the central nervous system by analysis of polypeptide patterns in spinal fluid. Prior to the development of this invention's silver stain for polypeptides, about 40 polypeptide bands could be visualized. It is now possible to identify over 400 polypeptide species with the stain method of this invention.

(4) Visualization of polypeptide hormones and quantitation of their levels when appropriate, in serum, spinal fluid indurine, etc.

(5) Analysis of cellular polypeptide patterns for genetic, physiological and/or pathophysiological studies.

(6) Polypeptide purification by defining contaminants at lower levels than was possible previously.

(7) Detection of polypeptides present in low levels, in urine and spinal fluid, without the necessity of extensive concentration.

(8) Use of the stain methods of this invention in conjunction with high-resolution polypeptide mapping methods to facilitate the evaluation of metabolic events, pathophysiological processes, and the detection of mutations.

(9) Evaluation of drug therapy on metabolic pathways, as monitored by polypeptide concentrations.

(10) Diagnosis of neoplastic diseases by observation of characteristic polypeptides associated with malignant cells.

(11) Use of the stain method of this invention in conjunction with analytic techniques generally, especially where the polypeptide content of the evaluation sample is small.

(12) Polypeptide (protein) assays by precipitation of polypeptides onto filter paper (especially cellulose nitrate paper) and staining with the method of this invention. Fixation may not be required, but the stain procedure is otherwise the same.

(13) Histological (tissue) staining may be done with the method of this invention. Staining of a tissue slice, such as may be produced by a biopsy, etc., is particularly sensitive when conducted according to the method of this invention.

(14) Chromosomes may be stained using the method of this invention. It would be possible to distinguish banding patterns with more sensitivity and possibly to show additional bands. This would be of particular use in prenatal diagnosis and in the positive and comparative identification of particular cells.

EXAMPLES

EXAMPLE 1 (A silver stain according to this invention).

Polypeptides were separated by the two-dimensional electrophoretic method developed by O'Farrell and disclosed in J. Biol. Chem. 250, 4007–4021 (1975). The second dimension gels of 10% acrylamide were 16×12 cm, and 0.8 mm thick. Polypeptides were fixed and excess sodium dilauryl sulfate removed from the gels by three 200 ml, 10 minute rinses with an aqueous mixture of ethanol (10%) and acetic acid (5%).

The polypeptide-gels were then soaked for 5 minutes in a 200 ml solution of 0.034 M potassium dichromate and 0.032 N nitric acid. The gels were washed 3 times, for two minutes each time, in 200 ml deionized water, and placed in 200 ml of 0.012 M silver nitrate for 20 minutes. This was followed by rinsing rapidly with two 300 ml aliquots of the image developer solution which contained 0.21 M sodium carbonate and 0.5 ml of commercial formaldehyde per liter. The gels were gently agitated in a third aliquot of this solution until the image had reached the desired intensity. Development was stopped by discarding the developer and adding 100 ml of 0.2 acetic acid. The gels were washed twice with 200 ml of water before storage and sealed in plastic bags. Maximal sensitivity is achieved if the gel is exposed to relatively intense uniform light or heat during the first minutes in silver nitrate. A fluorescent light source of uniform intensity gave the best results. It was found that some sensitivity is lost when gels are greater than 1 mm thick.

The silver stain of this invention was demonstrated to be at least equal and perhaps somewhat more sensitive than the histologically derived silver stain (FIG. 1). Densities obtained with the two stains were proportional over a wide range of protein concentrations. Polypeptide "spot" counts made on two-dimensional gels established that the photochemical silver stain was at least as efficient as the histological stain in detecting the presence of polypeptides in gels. Both stains displayed the same specificity for polypeptides. Treatment of E. coli or human cell lysates with protease k (an enzyme which degrades polypeptides) resulted in the disappearance of all discrete spots on the gels.

Figure 2:
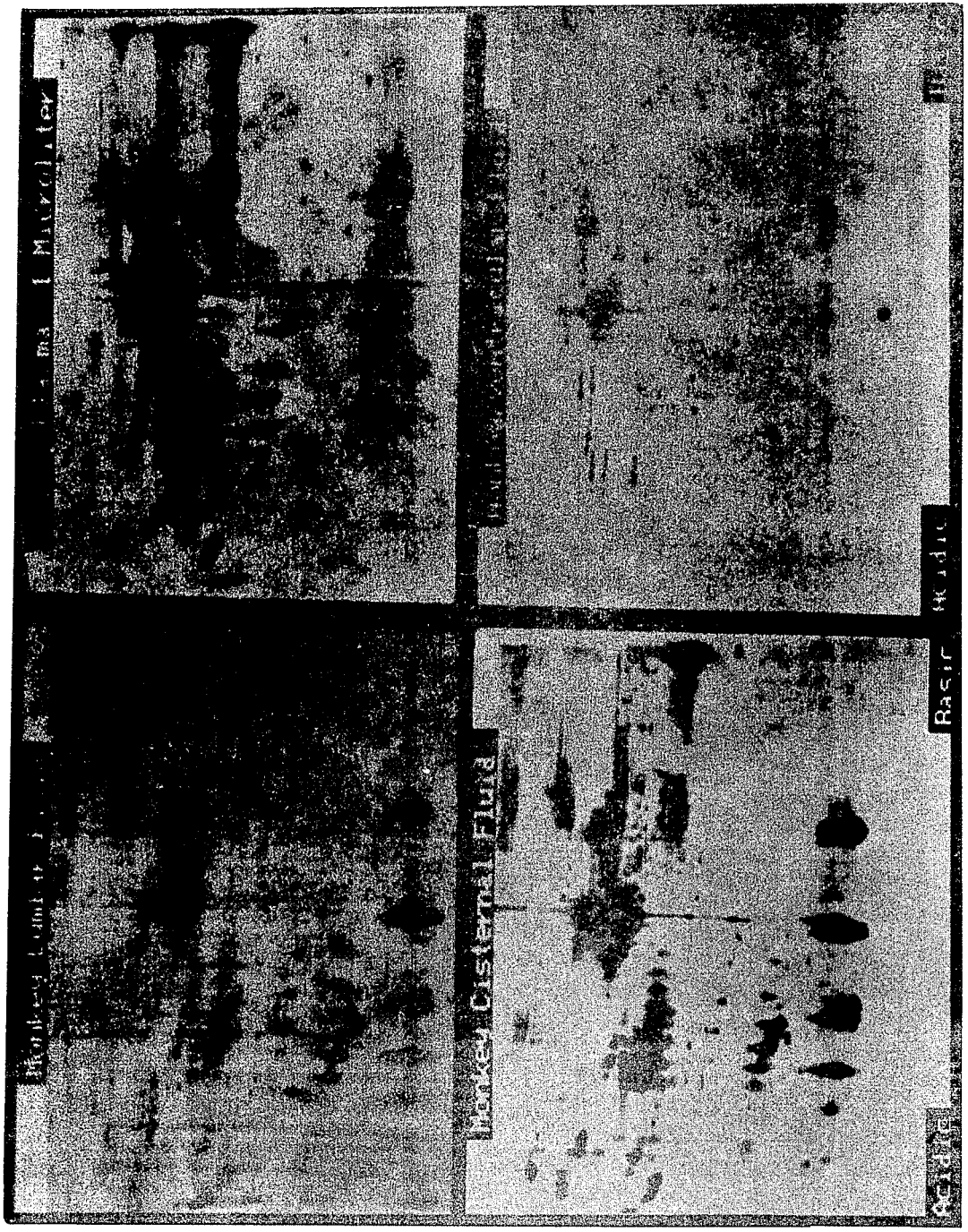
FIG. 2 is a photograph of two-dimensional electrophoretic gels containing polypeptides, stained by the method of this invention.
Figure 3:
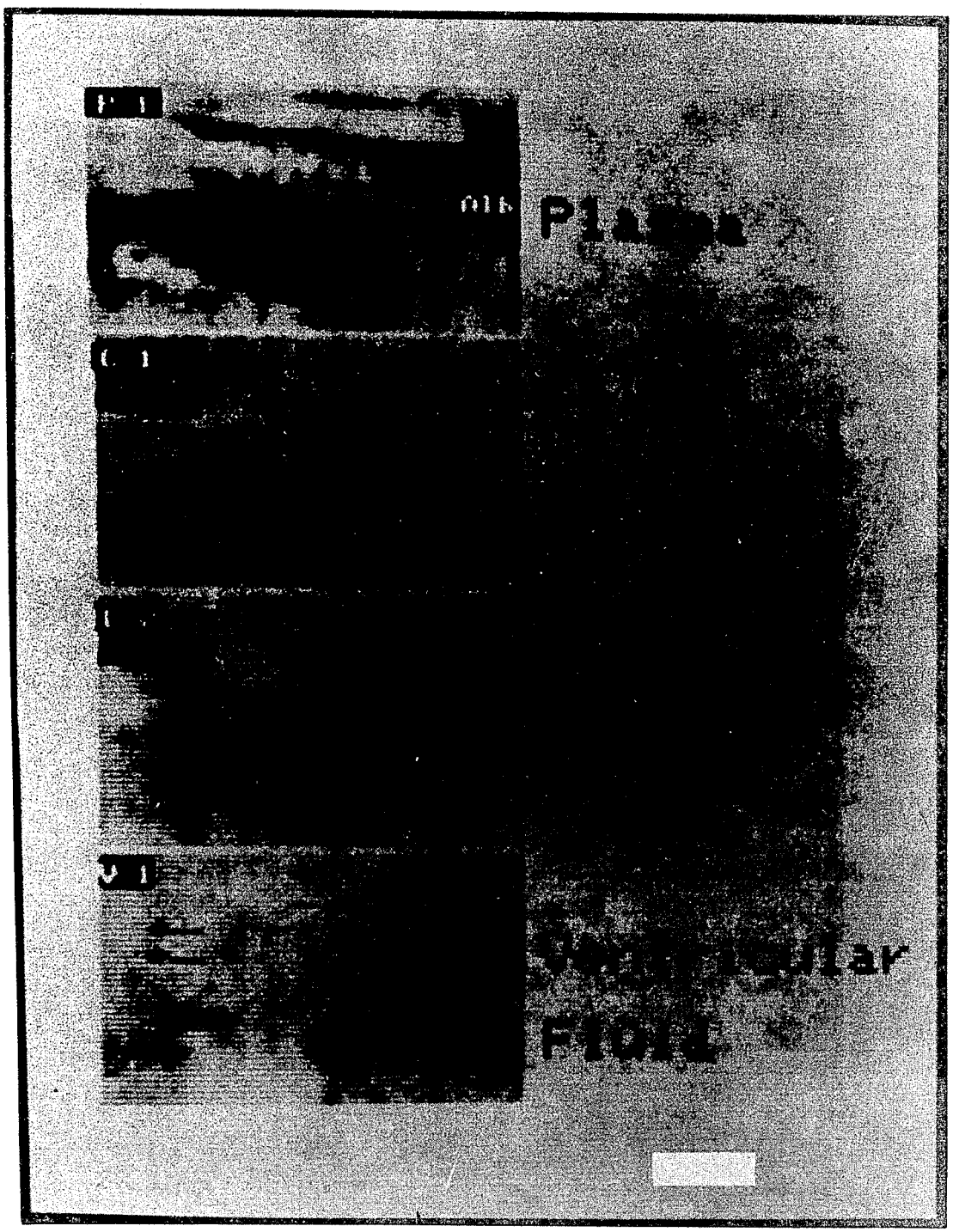
FIG. 3 is a composite photograph of an enlarged subregion of the gels shown in FIG. 2.

The utility of the stain is illustrated in FIGS. 2 and 3 in which two-dimensional electrophoretic patterns of primate cerobrospinal fluid (CSF) from various regions and of plasma are presented. CSF was obtained from 6 Rhesus macaque, from the lateral ventricle, cisterna magna, and lumbar space. Quantitative differences were noted in the distribution of a number of polypeptides, including albumin, α1-antitrypsin haptoglobin, immunoglobulin G (light and heavy chains), Gc globulin, α2 HS glycoprotein, α1-antichymotrypsin, α1-β-glycoprotein and transferrin, with lower concentrations in CSF from the lateral ventricle. Some CSF polypeptides not seen in plasma were also noted to be present in lower concentration in lateral ventricle CSF. However, other CSF polypeptides, several of which are indicated in the Figures by arrows, were not distinguished in lateral ventricular CSF, demonstrating that individual polypeptide variations occur in the subregions of CSF.

Hill, McKenyie, McGuckin, Goldstein, and Saview, in Proc. Mayo Clin., 33, 686–698 (1958) demonstrated a gradient in cerebrospinal fluid for albumin, prealbumin, and 4 globulin fractions using one-dimensional electrophoresis. These investigators found that the concentrations of albumin and four globulin fractions were lower in ventricular CSF, which had a higher relative concentration of prealbumin. Using immunological techniques, others have identified 9 antigenic species in CSF which are absent in serum. Recently, a method for preparative separation of CSF-specific proteins by affinity chromatography and isoelectric focusing was described. Silver-stained two-dimensional electrophoretic gels, according to this invention, permit the quantitative evaluation of more than 300 polypeptides in CSF and the direct visualization of protein variations in CSF and other tissues and fluids.

FIG. 1, referred to above, is a comparison of the original histochemically derived stain [according to Switzer, Merril and Shifrin (1979)] with the improved silver stain of Example 1 of this invention. This is a density versus density plot of all polypeptide spots within a small subregion of an E. coli lysate gel pattern. The slope was 1.08, the Y intercept −8.1 and the correlation coefficient 0.94. Gels were positioned next to a National Bureau of Standards calibrated photographic density standard and photographed with Tri-X 120 mm film(Kodak). These photographic images were then scanned at 100 microns resolution using a 1000 HS scanning densitometer (Optronics International Inc., Chelmsford, Mass. U.S.A.). Image densities were converted to optical density units using the calibrated density standard. This conversion normalized gel images for the significant variations in photography and scanning densitometry. Measurements were made with a IP5000 image processor (DeAnza Systems Inc., San Jose, Calif.) and PDP 11/60 computer (Digital Equipment Corp., Marlboro, Mass., U.S.A.) using background subtraction and identical measurement windows. The original gel pattern was produced by subjecting 10 μg of E. coli lysate proteins to two-dimensional gel electrophoresis according to the above mentioned method of O'Farrell.

FIG. 2, referred to above, demonstrates two-dimensional electrophoretic patterns of primate cerobrospinal fluid and plasma stained with the improved silver stain of Example 1 of this invention. Samples were obtained from individual adult Rhesus macaque by lumbar or cisternal puncture or by cannulation of the lateral ventricle or by veinpuncture. CSF samples were concentrated four fold by dialysis against 10% polyethylene glycol at 4°0 C. 15 microliters of each concentrated CSF sample and 1 microliter of plasma were electrophoresced. In the Figure, the arrows on the ventricular CSF pattern indicate polypeptides which are relatively more concentrated in ventricular CSF.

FIG. 3, referred to above, is a composite of an enlarged subregion of the gels shown in FIG. 2. This is the region in which the largest differences in polypeptide patterns are observed. The arrows in the Figure indicate polypeptides which are relatively more concentrated in ventricular CSF.

EXAMPLE 2 (Conventional sample preparation and electrophoresis)

Sample preparation: Human peripheral blood lymphocytes were obtained by venipuncture under sterile conditions in heparinized tubes. Lymphocytes were isolated by centrifugation at 450×G for 40 minutes in a Ficoll-Hypaque gradient. These cells were washed twice with phosphate-buffered saline (pH 7.4), pelleted and then subjected to three cycles of freeze-thawing. A lysis solution (100 microliters/sample) containing 2% sodium dilauryl sulfate, 5% mercaptoethanol, 20% glycerol, 2% Biolyte 3/10 (Bio-Rad, Richmond, Calif., U.S.A.), and 2% Nonidet P-40 (BRL, Bethesda, Md., U.S.A.) was added and the sample heated at 95° C. for 5 minutes. After heating, the sample was rapidly cooled in an ice bath, brought to room temperature and centrifuged at 12,000×G for 2 minutes. The supernatant was stored at −70° C. Plasma samples were prepared from heparinized venous blood by heating with six volumes of lysis solution to denature the proteins and were then stored at −70° C.

Electrophoresis: Two-dimensional electrophoresis of lymphocyte and *E. coli* proteins was accomplished according to the procedure of O'Farrell. A mixture of 1.6% (5-7) and 0.4% (3–10) ampholines was used for the isoelectric focusing, which was carried out at 500 volts for 20 hours. A 10% uniform acrylamide gel (0.8 mm thick) and a 4.75% acrylamide stacking gel were used for the second dimension, which was run at 20 mA/gel. Plasma protein standards were prepared by mixing 5 microliters of denatured plasma with 10 microliters of 20% glycerol and placing this solution into a trough at the top of a PAGE gel in the presence of 0.1% SDS. After electrophoresis at 20 mA, the gel was sliced into strips cut parallel to the direction of electric flow, fixed with methanol (50%) and acetic acid (12%) and stored for use. Purified, denatured, low and high molecular weight marker proteins were placed in preformed wells and polyacrylamide gel electrophoresis was carried out in a manner similar to the plasma proteins.

Staining: A conventional histochemically-derived stain was performed as described by Switzer, Merril and Shifin (1979), above, to contrast and compare it with the more recently developed improved methods of silver staining according to this invention. The histochemical stain is based on the copper-silver method of de Olmos as described at *Brain Behav. Eval.*, 2, 213–237 (1969). It required 3 hours to perform and 915 grams of silver per gel.

EXAMPLE 3 (An improved silver stain according to this invention)

(1) polypeptide sample infused gels were fixed in a 10% methanol and 5% acetic acid solution and then washed twice for ten minutes with this same solution to remove residual sodium dilauryl sulfate;

(2) the gels were then soaked 5 minutes in 200 ml of a solution of 0.03 M potassium dichromate and 0.0016 N nitric acid, followed by 3 rinses, for two minutes each, in 200 ml deionized water;

(3) the gels were then soaked in 0.012 M silver nitrate (200 ml) for 20 minutes while illuminated with a bright uniform source; and (4) the silver nitrate was discarded and the gels rapidly rinsed with two 300 ml aliquots of the image developer, which contained an aqueous solution of 0.3 M sodium carbonate and 0.5 ml of commercial formaldehyde per liter. The gels were then gently agitated in a third aliquot of developer until the image reached the desired intensity (about 15 minutes). When staining was complete, the developer solution was discarded and the gels were washed extensively with distilled water or put in a 0.2 N acetic acid stop solution for five minutes and then washed with distilled water.

Densitometry: The gels were photographed next to a stepped density standard (as an aid for normalization of gel densities) on 120 mm Tri-X film (Kodak). The negatives were scanned with a P-1000HS scanning densitometer (Optronics International, Inc., Chelmsford, Mass.) at 100 microns resolution using the "3D" optical density range. The data was processed with a PDP 11/60 computer equipped with a DeAnza IP5000 image processor. Identical gel regions were measured for particular polypeptide bands and spots. The density standard on the negative was used to normalize the computer images to correct for variations in photographic and scanning techniques. Backgrounds were estimated by subtracting the low density value near the polypeptides or, in some experiments, by constructing a density histogram of the gel subregion and identifying the modal density. To measure the extent of polypeptide bands, the area of the band with density greater than the background density (as determined by the density histogram) was computed.

Light effects were investigated using plasma gel strips. The light source for these experiments and for all staining was a 160 watt fluorescent grid lamp (Aristo Grid Lamp Products Inc., Washington, N.Y., U.S.A.) which emits light equivalent to a 1500 watt tungsten source.

Analysis of Examples 2, 3, and other experimental results

The staining of polypeptides according to the improved silver staining method of this invention is a process which is, in practice, greatly affected by three variables: light exposure, polypeptide concentration, and time of development. When intense exposure to light during the silver nitrate step was omitted, polypeptide spot densities were less than 50% of the densities obtained in an equivalent gel with intense light exposure. Using a saturating light exposure, it was found that no increase in sensitivity occurred after 5 minutes of exposure with the light source.

Figure 4:
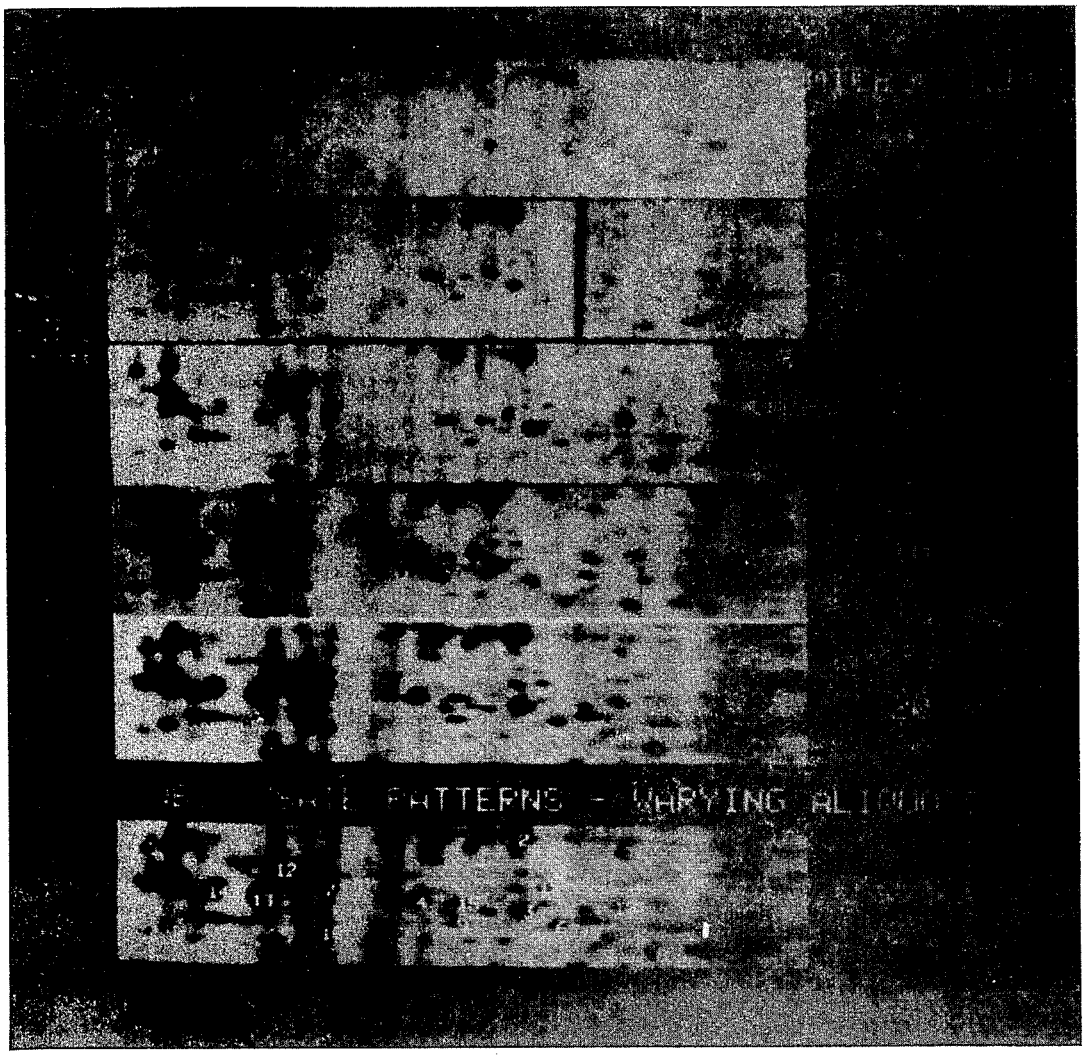
FIG. 4 is a comparison photograph of stains according to this invention with different polypeptide concentrations.

It was possible to stain gels with different polypeptide concentrations so that they approximated each other in density as shown in FIG. 4. Analysis of the total densities (minus background) of 45 individual polypeptides on these gels revealed that densities were proportional between gels as long as the difference between polypeptide loading was no greater than ten-fold. The relationship between polypeptide concentration and density was analogous to the relationship seen in photography between total light exposure and density. When an excessive amount of polypeptide mixture was applied, many polypeptides showed saturation of staining, just as regions, of a photographic negative may show saturation under conditions of excessive light exposure. This saturation of staining produced lower coefficients of correlation in density versus density plots. When smaller amounts of polypeptide mixtures are applied, more polypeptides fall in the linear portion of the polypeptide staining curve.

Analysis of stained purified polypeptides reveals that densities increase proportionally during development and that staining is linear from the limit of sensitivity (0.1 ng/m$^2$) to approximately 2 ng/m$^2$ when using gels 0.8 mm thick. A series of polypeptide concentration versus density curves, shown in FIG. 5, were generated by photographing the gels during development and then alalyzing the densities. A threshold effect for polypeptide concentration versus density was not seen. The density versus time curves for individual polypeptides are shown in FIGS. 6A and 6B, which illustrate the fact that the development of regions containing different concentrations of polypeptides proceeds along the same time course, so that ratios of polypeptide to polypeptide are not likely to alter drastically as development proceeds (provided that background density is subtracted).

As in photographic development, the slope of the linear portion of the development curve increases with increasing time of development. Once optimal staining is achieved (at 8-12 minutes in developer), further development only raises background levels, and eventually the entire gel may become dark.

Figure 7:
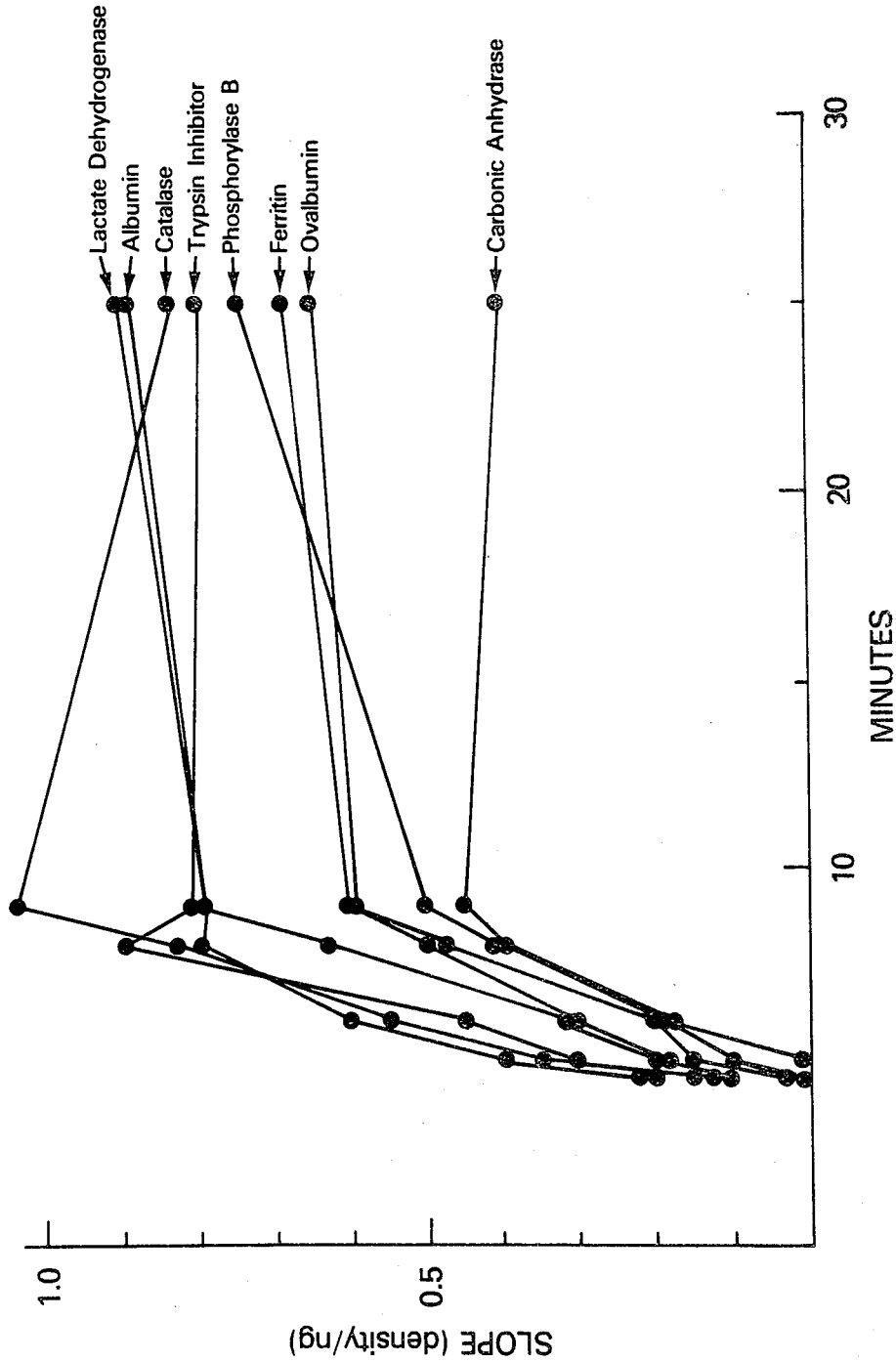
FIG. 7 is a curve demonstrating that for silver stained polypeptides according to this invention, there is an analogous increase in the slope of the density/polypeptide concentration with increasing time of development.

In photography, a "gamma curve" demonstrating the increasing slope of the density/light exposure relationship with increasing time of development can be generated. FIG. 7 demonstrates that for silver stained polypeptides according to this invention there is an analogous increase in the slope of the density/polypeptide concentration with increasing time of development. The slope of the density/polypeptide relationship increases linearly and in a constant manner for different polypeptides. The plateau seen in this particular experiment may be due to exhaustion of silver but not developer since replenishment of developer does not permit further image formation.

Figure 8:
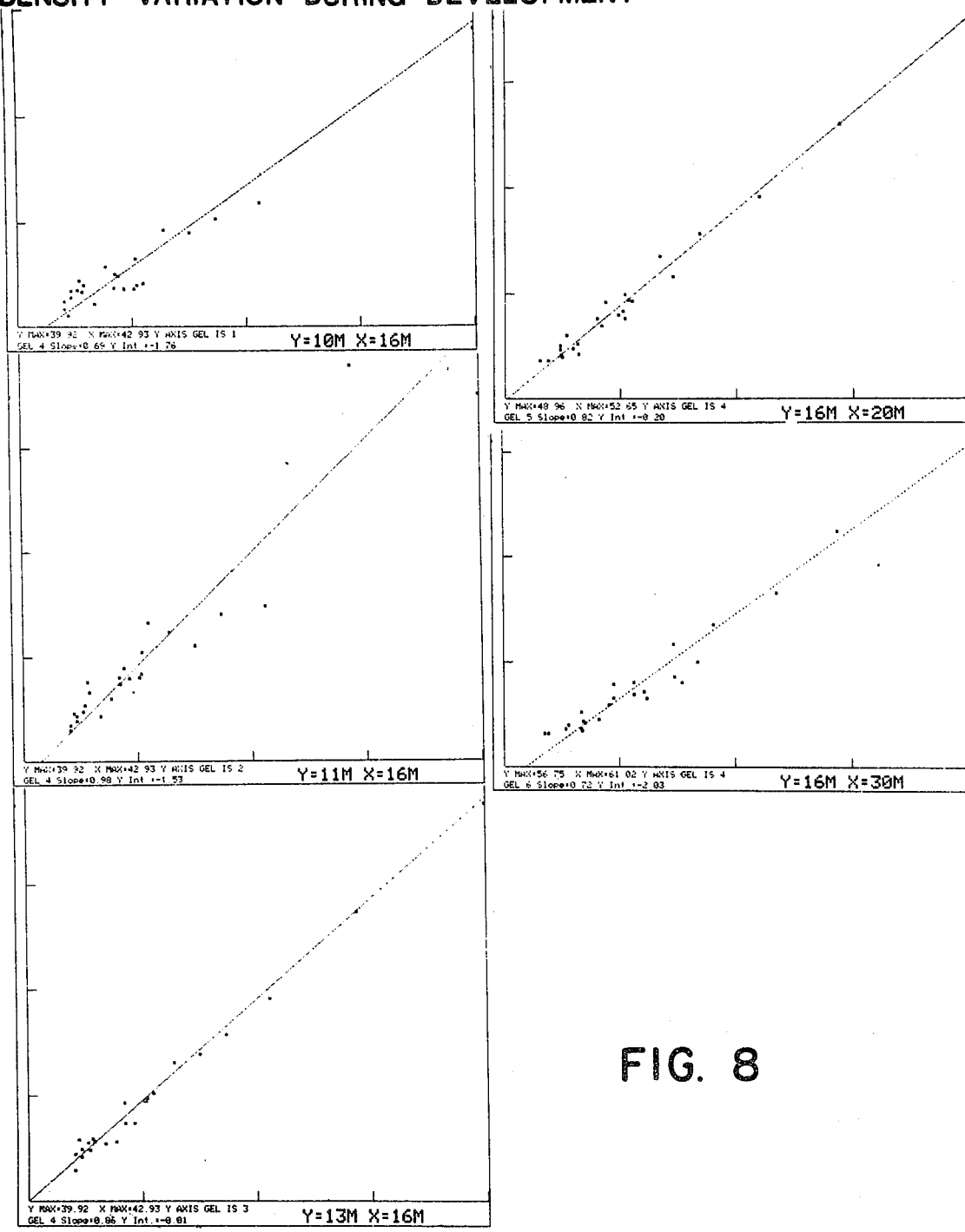
FIG. 8 is a curve showing density versus density correlation coefficients, with the passage of time.

These findings for individual purified polypeptides were reproduced in whole gel patterns. When an *E. Coli* lysate pattern was sequentially photographed during development and the densities of 25 polypeptide spots monitored, as shown in FIG. 8, density versus density correlation coefficients were greater than 0.90 between time points with a twofold difference in average polypeptide density.

Figure 9:
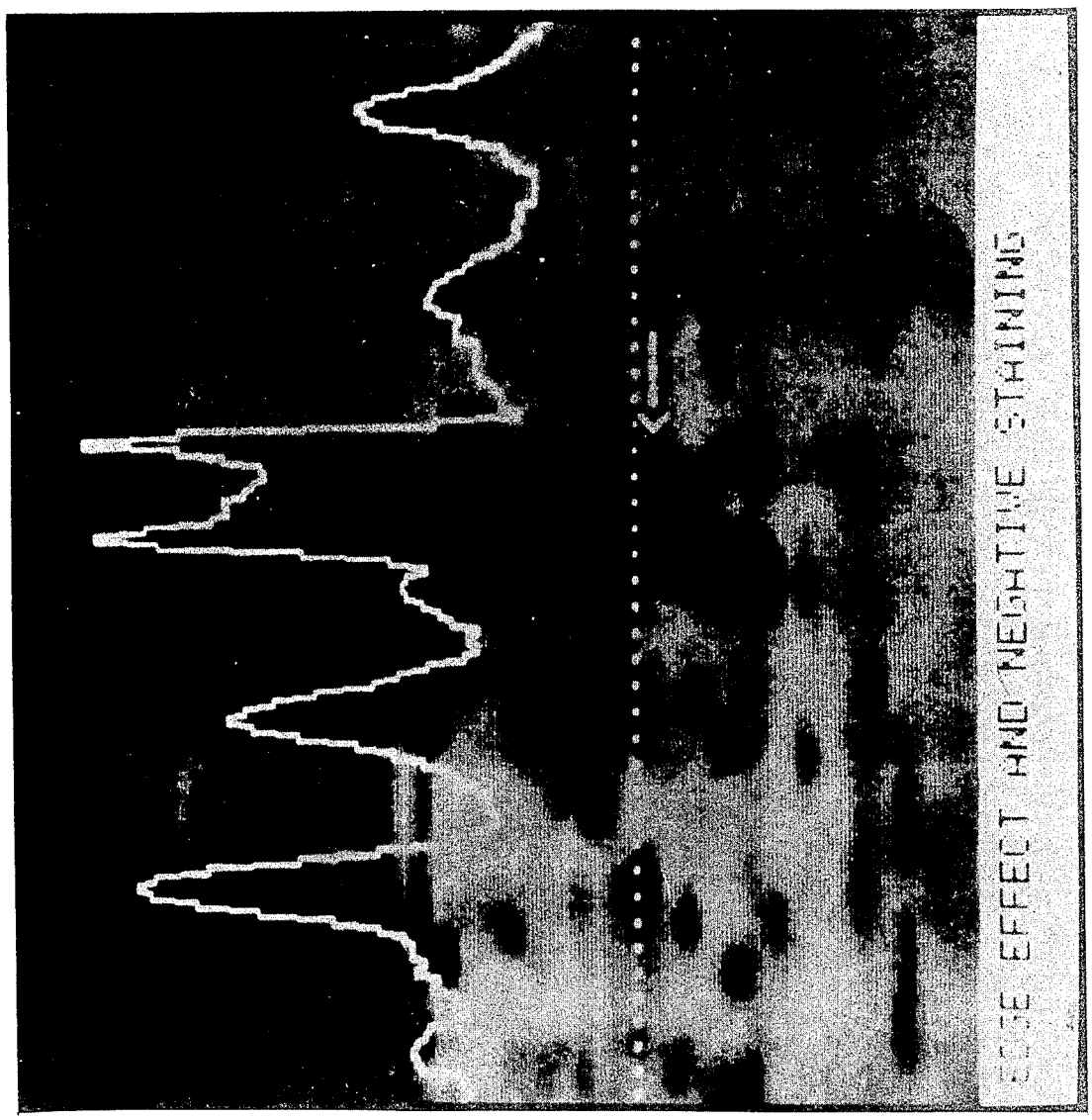
FIG. 9 is a photograph showing artifacts that may occur in the quantitative qualitative use of silver stains according to this invention.

Difficulties may occur in the quantitative or qualitiative use of silver stains, two of which are shown in FIG. 9. A region of lower density is occasionally noted in the middle of a dense polypeptide spot. Rarely, there may be a region of lower background adjacent to a dense spot. Similar artifacts were observed by early photographers who were forced to use thick emulsions which limited the efficiency of diffusion of fresh developer and of reaction products which might limit development. By increasing the time of development, such negative staining becomes less prominent and may disappear, but the background increases, the slope of polypeptide concentration versus density relationship increases, and the region of staining linearity is diminished. Saturation of staining, a type of which is negative staining, limits the concentration of polypeptide that can be quantitated in a spot or band (usually any concentration greater than 2 ng/mm$^2$). A third problem may occur with gels thicker than those used (0.8 mm). A separate image may develop on each side of the slab gel. This could be due to an accentuation of the diffusion problem discussed above or to an actual difference in the distribution of polypeptides within these thick gels.

Two-dimensional electrophoresis is becoming a valuable tool in physiology and genetics because of its ability to resolve hundreds of polypeptides in a single array. Quantitative analysis of these polypeptides depends on accurate, sensitive microdensitometric measurements of polypeptide "spots" whose densities are regularly related to polypeptide concentration. Methods of polypeptide visualization possessing this regularity include autoradiography, some methods using organic dyes and, as described herein, the silver stains of this invention. Successful quantitative analysis of these polypeptides must also depend on choice of the appropriate analytic strategy for intersample comparisons. Advantage was taken for this invention of the large number of polypeptides which are synthesized constitutively and are present in nearly constant quantities within a particular cell type or preparation. Such polypeptides may be said to serve as "internal standards." These constitutive polypeptides are first used as internal markers of charge and molecular weight so that these parameters can be accurately estimated for polypeptides of interest and for precise pairing of polypeptide spots in different gels. Then, after densitometric measurements have been made, constitutive polypeptides densities are used to normalize the densities obtained from any particular gel to the densities found in the reference gel. Correlation coefficients between gels for similar samples and as many as 700 individual polypeptides are usually greater than 0.92. The average error between equivalent spots on separate gels is 15-30%. Improvements in image visualization and quantitative densitometry are adding a third dimension to the analytic technique of electrophoresis.

FIG. 4, mentioned above, shows identical subregions of lymphocyte lysate gels for the purpose of illustrating the effect of loading different amounts of polypeptide. Lysates were prepared and electrophoresced as described above. The following amounts of polypeptide were loaded onto each gel: 200 μg (20 μl), 100 μg (10 μl), 50 μg (5 μl), 25 μg (2.5 μl), and 1 μg (1 μl). The total density (average density-background density)-×area of 45 individual polypeptide spots in each gel was compared to the corresponding spot density in each of the other gels. Correlation coefficients and slopes were as follows:

| Polypeptide μg | Coefficients Matrix | | | | | Slope Matrix | | | | |
|---|---|---|---|---|---|---|---|---|---|---|
| | 10 | 25 | 50 | 100 | 200 | μg | 10 | 25 | 50 | 100 | 200 |
| 10 | 1.00 | | | | | 10 | 1.00 | | | | |
| 25 | 0.94 | 1.00 | | | | 25 | 1.42 | 1.00 | | | |
| 50 | 0.95 | 0.96 | 1.00 | | | 50 | 1.61 | 1.07 | 1.00 | | |
| 100 | 0.90 | 0.94 | 0.97 | 1.00 | | 100 | 2.06 | 1.42 | 1.32 | 1.00 | |

-continued

| | | | | | | | | | | |
|---|---|---|---|---|---|---|---|---|---|---|
| 200 | 0.60 | 0.73 | 0.74 | 0.80 | 1.00 | 200 | 1.10 | 0.88 | 0.81 | 0.64 | 1.00 |

| Y Intercept Matrix | | | | | | Mean Spot Density | |
|---|---|---|---|---|---|---|---|
| Polypeptide μg | 1 | 2.5 | 5 | 10 | 20 | μg | D |
| 10 | 0.00 | | | | | 10 | 27.3 |
| 25 | 4.37 | 0.00 | | | | 25 | 43.0 |
| 50 | 7.76 | 5.51 | 0.00 | | | 50 | 51.6 |
| 100 | 13.7 | 8.67 | 1.85 | 0.00 | | 100 | 69.8 |
| 200 | 42.4 | 34.5 | 30.9 | 27.6 | 0.00 | 200 | 72.5 |

Figure 5:
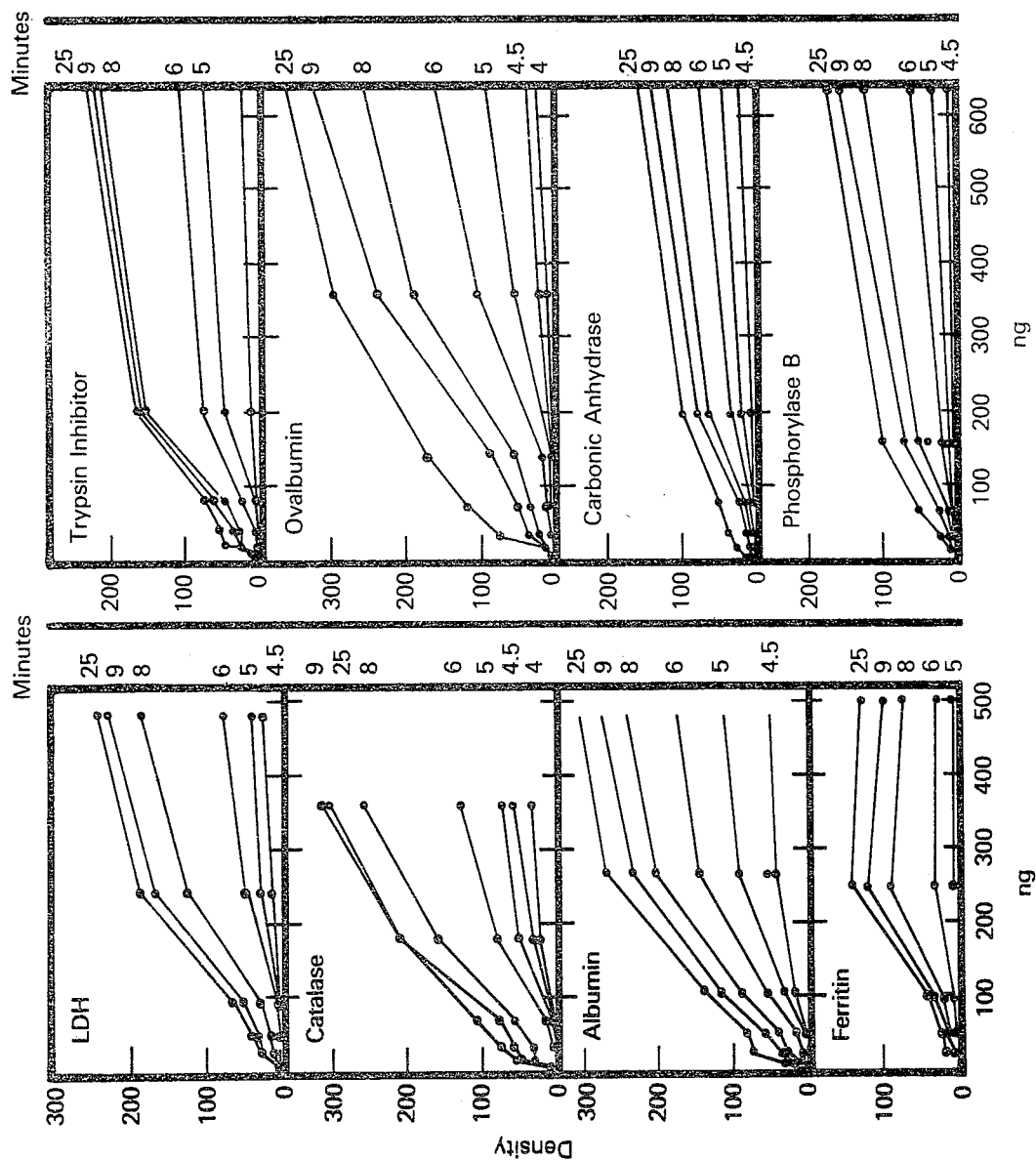
FIG. 5 is a series of polypeptide concentration versus density curves.

FIG. 5, discussed above, shows concentration versus density curves for eight polypeptides. Concentrations are here given in ng of polypeptide added per well. For comparison, polypeptide concentrations in FIG. 4 (same dilutions) are given in $\mu g/mm^2$. Backgrounds were subtracted after using a histogram to determine the modal density around each band.

Figure 6:
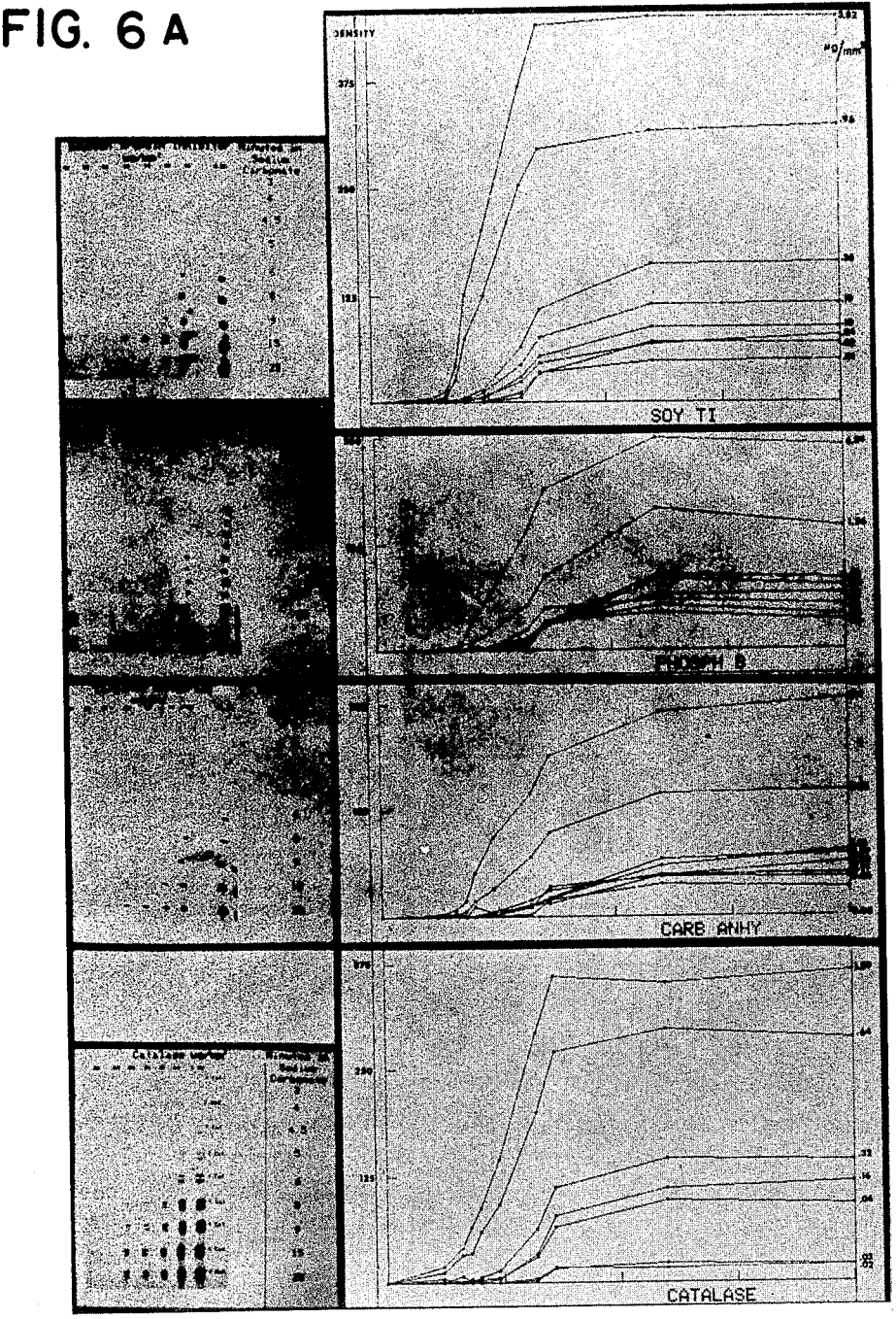
FIGS. 6A and 6B are a series of density versus time curves for individual polypeptides.
Figure 6B:
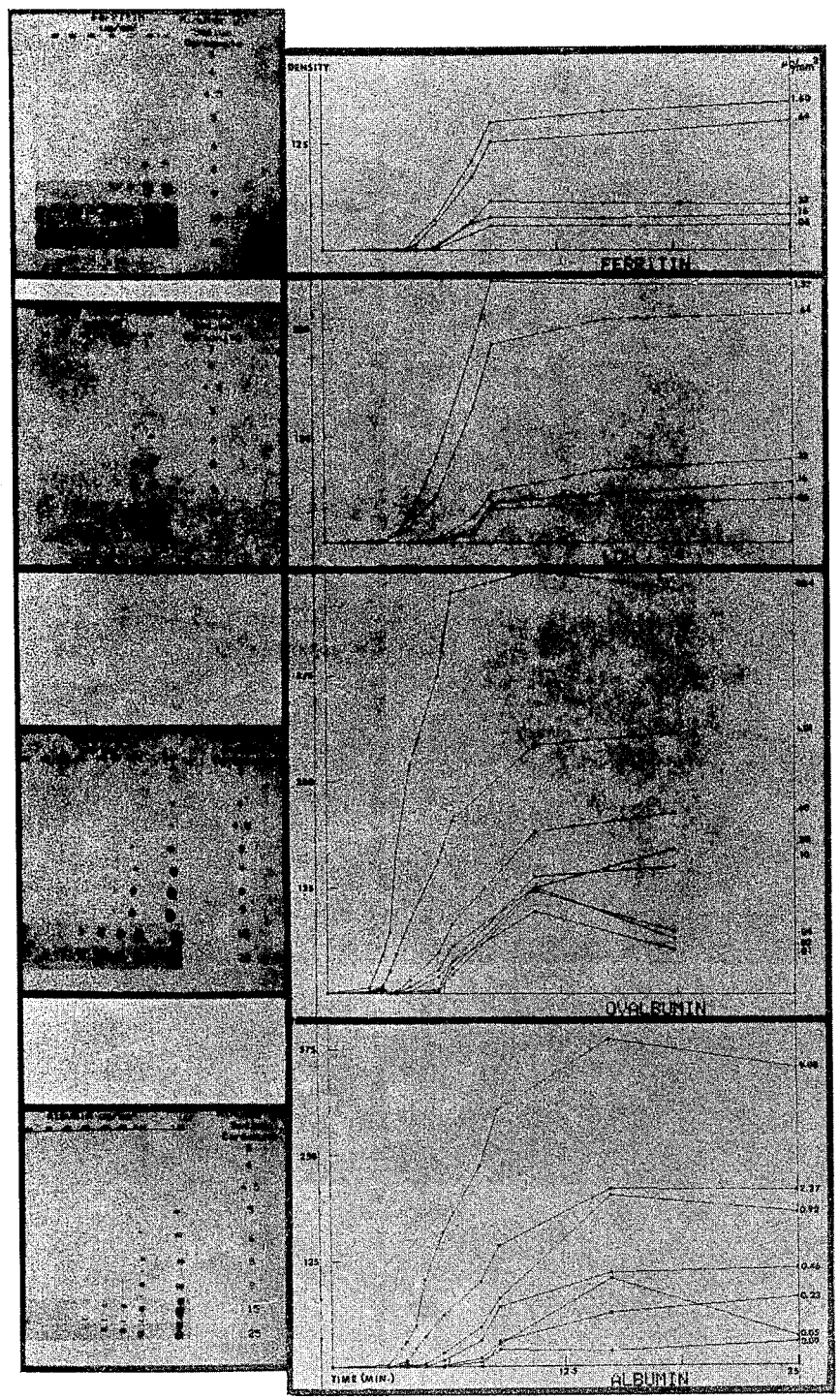

FIG. 6, discussed above, shows concentration (density) versus time of development curves for individual polypeptides. Polypeptide concentrations are given here in $\mu g/mm^2$.

FIG. 7, discussed above, shows variation of slope of the polypeptide versus density relationship with increasing time of development in sodium carbonateformalin. Slopes were measured between 100 and 200 ng of protein for the eight different purified polypeptides.

FIG. 8, discussed above, shows sequential development of an *E. coli* lysate pattern. Lysate polypeptides were electrophoresced and the images analyzed as described above. Density measurements were made on 25 polypeptide spots. Statistical data were as follows:

| Coefficients Matrix | | | | | | Slope Matrix | | | | | |
|---|---|---|---|---|---|---|---|---|---|---|---|
| Min. in Na Carbonate | 11 | 13 | 16 | 20 | 30 | Min. in Na Carbonate | 11 | 13 | 16 | 20 | 30 |
| 11 | 1.00 | | | | | 11 | 1.00 | | | | |
| 13 | 0.94 | 1.00 | | | | 13 | 1.42 | 1.00 | | | |
| 16 | 0.95 | 0.96 | 1.00 | | | 16 | 1.61 | 1.07 | 1.00 | | |
| 20 | 0.90 | 0.94 | 0.97 | 1.00 | | 20 | 2.06 | 1.42 | 1.32 | 1.00 | |
| 30 | 0.60 | 0.73 | 0.74 | 0.80 | 1.00 | 30 | 1.10 | 0.88 | 0.81 | 0.64 | 1.00 |

| Y Intercept Matrix | | | | | | Means | |
|---|---|---|---|---|---|---|---|
| Min. in Na Carbonate | 11 | 13 | 16 | 20 | 30 | Min. in Na Carbonate | Mean Density |
| 11 | 0.00 | | | | | 11 | 27.27 |
| 13 | 4.37 | 0.00 | | | | 13 | 43.00 |
| 16 | 7.76 | 3.31 | 0.00 | | | 16 | 51.63 |
| 20 | 13.7 | 8.67 | 1.85 | 0.00 | | 20 | 69.75 |
| 30 | 42.4 | 34.5 | 30.9 | 27.6 | 0.00 | 30 | 72.50 |

FIG. 9, discussed above, shows antifacts seen with the silver stain of this invention. This is a subregion of a lymphocyte lysate pattern. A plot of density has been made across this gel, as indicated by the dotted line. The double peak is due to a polypeptide spot with an internal region of lower density.

EXAMPLE 4 (polypeptide assay)

Polypeptides were precipitated with potassium dichromate and then filtered using cellulose nitrate filter paper under partial vacuum. The polypeptide source was purified bovine serum albumin, and the amounts tested ranged from 0.1 μg to 100 μg. After filtration, the polypeptides were successfully stained according to the preferred method of this invention. The fixing step was eliminated because no gel was used, but it is noted that the potassium dichromate used as an oxidant in the photoreversal step also acts as a fixative. The resultant stains were successful and sufficiently sensitive to indicate that this embodiment of the stain method of this invention could be used for quantitative polypeptide assays, by comparing the stain intensity to a standard.

EXAMPLE 5 (tissue stains)

Thin tissue slices were successfully stained with the silver stain method of this invention. This embodiment shows that the method of this invention can readily be adapted to provide improved histological stains. This embodiment would be useful for biopsies.

EXAMPLE 6 (optimum stain procedure)

A stain was prepared in accordance with the optimum embodiments of this invention in the following manner. Where unspecified, the quantities are as otherwise stated in this specification.

1. Fix gel in trichloroacetic acid or in a methanol/acetic acid solution.
2. Wash three times with 10% ethanol-5% acetic acid solution.
3. Soak gel 5 minutes in 0.0034 M potassium dichromate and 0.0032 N nitric acid.
4. Soak gel 20 minutes in 0.012 M silver nitrate.
5. Rinse gel with agitation in a solution containing 0.28 M sodium carbonate and 0.5 ml formaldehyde. This last step requires at least two changes of solution to prevent precipitated silver salts from contaminating the gel surface.
6. Stop the stain by washing the gel for 5 minutes in 3% acetic acid, before development of the background.

Up to this point, the stain procedure is as in the previous examples, except that activating irradiation is not used. In an optimum embodiment of this invention, then 7. Wash the gel two more times for 5 minutes each time in a 3% acetic acid solution. and
8. Repeat above steps 4 through 6 at least once.

Using the above procedure, experiments utilizing two-dimensional electrophoretic protein patterns from E. coli gels revealed a doubling of sensitivity with the first recycling (20 proteins were measured on each gel for each cycle).

| No. of times steps 4-6 were undertaken | Mean protein spot density | Mean background |
| --- | --- | --- |
| 1 | 10.23 | 0.432 |
| 2 | 20.21 | 0.581 |
| 3 | 26.63 | 1.105 |

From the above, it can be seen that the Mean protein spot density desireably rises with repeats of steps 4-6, but that the Mean background undesireably also rises. Thus, steps 4-6 should preferably be conducted from one to three times, most preferably twice. The increased Mean protein spot density permitted a number of proteins which originally were very faint to be easily identified.

What I claim is:

1. A silver stain method for polypeptides fixed in gels comprising the sequential steps without substantial non-ambient illumination of
   photo-reversing the polypeptide-gel by treatment with an oxidizing agent,
   forming a latent stain image by treating the polypeptide-gel with a photosensitive salt, and
   developing the stain image by treating the polypeptide-gel with a reducing agent.

2. The method of claim 1 wherein the steps of forming the latent stain image followed by developing the stain image are repeated at least once.

3. The method of claim 2 wherein the polypeptides in gels have been subjected to electrophoresis prior to staining.

4. The method of claim 2 wherein the steps are repeated once.

5. The method of claim 2 wherein
   the gel is selected from at least one of the group consisting of polyacrylamide, agarose, and cellulose acetate,
   the polypeptide is fixed by a stain fixing means,
   the oxidizing agent is selected from at least one of the group consisting of acid dichromates, potassium permanganate, molecular oxygen, potassium ferricyanide, iodine, and quinone,
   the photosensitive salt is selected from at least one of the group consisting of silver, gold, platinum, paladium, and iridium photosensitive salts, and
   the reducing agent is selected from at least one of the group consisting of: metallic compounds of iron, tungsten, vanadium and molybdenum; hydroquinone, pyrogallol, p-aminophenol, p-phenylenediamine, paraformaldehyde, and formaldehyde.

6. The method of claim 5 wherein
   the gel is a polyacrylamide gel,
   the oxidizing agent is selected from the group consisting of dichromates and molecular oxygen,
   the photosensitive salt is a silver salt, and
   the reducing agent is selected from at least one of the group consisting of hydroquinone, pyrogallol, p-aminophenol, p-phenylenediamine, paraformaldehyde, and formaldehyde.

7. The method of claim 6 wherein
   the oxidizing agent is an aqueous potassium dichromate solution containing a small amount of nitric acid,
   the photosensitive salt is silver nitrate, and
   the reducing agent is paraformaldehyde, formaldehyde, or their mixture.

8. The method of claim 5 wherein the fixing is with an agent selected from at least one of the group consisting of glutaraldehyde, mercury oxide, lead oxide, osmium oxide, formaldehyde, paraformaldehyde, trichloroacetic acid and acetic acid.

9. The method of claim 8 wherein the fixing agent is selected from the group consisting of trichloroacetic acid, formaldehyde, paraformaldehyde, and acetic acid.

10. The method of claim 9 wherein the fixing agent is acetic acid (about 5-20%) and is employed in an aqueous mixture with methanol and/or ethanol (about 10-50%).

11. The method of claim 5, 6, 7 or 9 wherein
    the fixing is by immersion of the polypeptide-gel in a stain fixing agent from 1 to 3 times for about 5 to 15 minutes each time,
    the treatment with the oxidizing agent is by immersion of the fixed polypeptide-gel therein for about 3 to 10 minutes,
    the treatment with the photosensitive salt is by immersion of the rinsed polypeptide-gel therein for about 10-30 minutes, and
    the treatment with the reducing agent is by at least one immersion therein for a period of about 10-20 minutes.

12. A silver stain method for polypeptides comprising the sequential steps without substantial non-ambient illumination of
    mixing the polypeptides with an aqueous solution of a fixing agent to form a polypeptide precipitate,
    filtering the mixture with filter paper,
    photoreversing the polypeptide precipitate by treatment with an oxidizing agent,
    forming a latent stain image by treatment of the polypeptide precipitate with a photosensitive salt, and
    developing the stain image by treatment of the polypeptide precipitate with a reducing agent.

13. A silver stain method for fixed tissue comprising the sequential steps without substantial non-ambient illumination of
    photoreversing a fixed tissue specimen by treatment with an oxidizing agent,
    forming a latent image by treating the tissue with a photosensitive salt, and
    developing the stain image by treating the tissue with a reducing agent.

14. A silver stain method for polypeptides fixed in gels comprising the sequential steps of
    photo-reversing the polypeptide-gel by treatment with an oxidizing agent selected from the group consisting of dichromates, potassium permanganate, molecular oxygen, iodine, and quinone,
    forming a latent stain image by treating the polypeptide-gel with a photosensitive salt,
    subjecting the polypeptide-gel to actuating irradiation by exposure to relatively intense uniform light during the first minutes of treatment with the photosensitive salt, and
    developing the stain image by treating the polypeptide-gel with a reducing agent.

15. The method of claim 14 wherein
    the gel is a polyacrylamide gel,
    the oxidizing agent is selected from the group consisting of dichromates and molecular oxygen,
    the photosensitive salt is a silver salt, and the reducing agent is selected from at least one of the group consisting of hydroquinone, pyrogallol, p-aminophenol, p-phenylenediamine, paraformaldehyde, and formaldehyde.

16. The method of claim 15 wherein the oxidizing agent is aqueous potassium dichromate solution containing a small amount of nitric acid, the photosensitive salt is silver nitrate, and the reducing agent is paraformaldehyde, formaldehyde, or their mixture.

* * * * *